United States Patent [19]

Santy

[11] 4,280,490

[45] Jul. 28, 1981

[54] UNIVERSAL SPLINT

[76] Inventor: James L. Santy, Box 783, 1362 Woodside Ave., Park City, Utah 84060

[21] Appl. No.: 98,672

[22] Filed: Nov. 29, 1979

[51] Int. Cl.³ ............................................. A61F 5/04
[52] U.S. Cl. ..................................... 128/88; 128/87 R
[58] Field of Search ............... 128/88, 87 R, 83, 84 R, 128/84 B, 77, 78, 80 R, 80 F, 94, 89 R

[56] References Cited

U.S. PATENT DOCUMENTS

| | | | |
|---|---|---|---|
| 1,639,815 | 8/1927 | Siebrandt | 128/88 |
| 1,803,566 | 5/1931 | Nugent | 128/94 |
| 2,229,271 | 1/1941 | Anderson | 128/87 R |
| 2,237,252 | 4/1941 | Longfellow | 128/87 R |
| 2,310,566 | 2/1943 | Anderson | 128/88 |
| 2,339,515 | 1/1944 | Parcher | 128/87 R |
| 3,528,413 | 9/1970 | Aydt | 128/90 |
| 4,019,504 | 4/1977 | Sterling | 128/88 |
| 4,034,748 | 7/1977 | Winner | 128/87 R |

FOREIGN PATENT DOCUMENTS

| | | | |
|---|---|---|---|
| 101512 | 11/1923 | Switzerland | 128/78 |
| 105419 | 4/1917 | United Kingdom | 128/88 |

*Primary Examiner*—Robert W. Michell
*Assistant Examiner*—Arthur S. Rose
*Attorney, Agent, or Firm*—M. Reid Russell

[57] ABSTRACT

A universal splint for use in immobilizing a body extremity or extremities that consists of a backboard with strap fasteners for securing it across a person's back. The backboard includes an elongate track formed thereacross wherein at least one locking pivot is arranged to travel that is arranged through one end of a first or pivot board. The opposite pivot board end connects through an upper double hinge arrangement to an upper arm board that connects, in turn, through a lower double hinge arrangement to a second or forearm pivot board, which forearm pivot board connects to a forearm board. The upper arm and forearm boards include strap fasteners for attachment to a persons injured extremity. The double hinge and pivot arrangements provide freedom of movement of individual board so as to be capable of being adjusted to a person's injured extremity for splinting that extremity in place, which double hinge and pivot arrangements are individually lockable.

11 Claims, 8 Drawing Figures

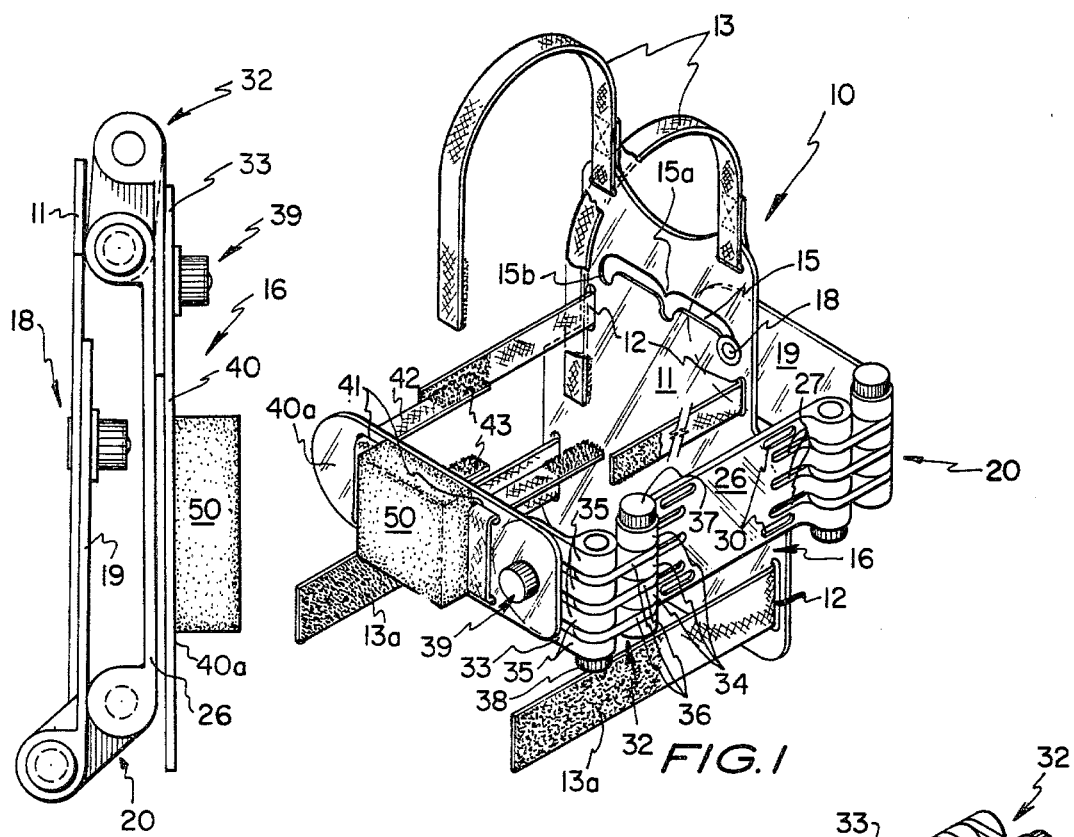
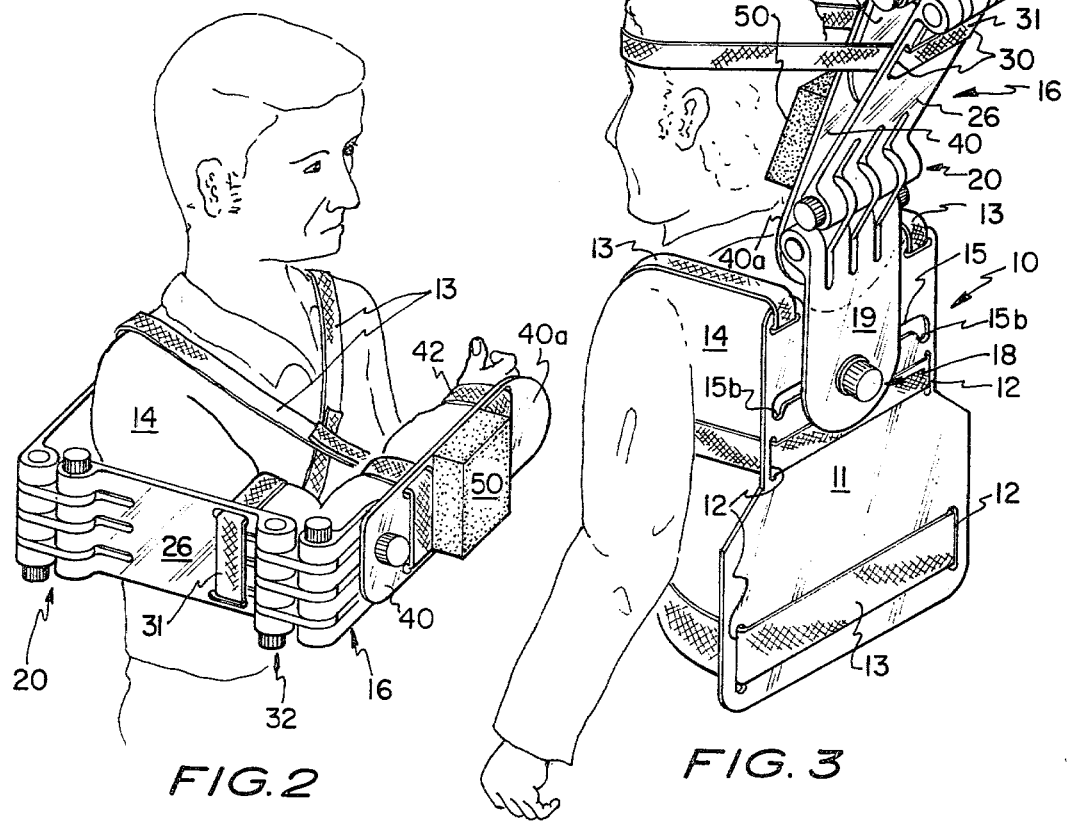

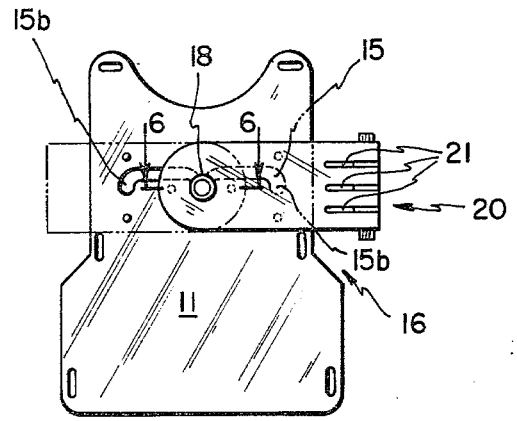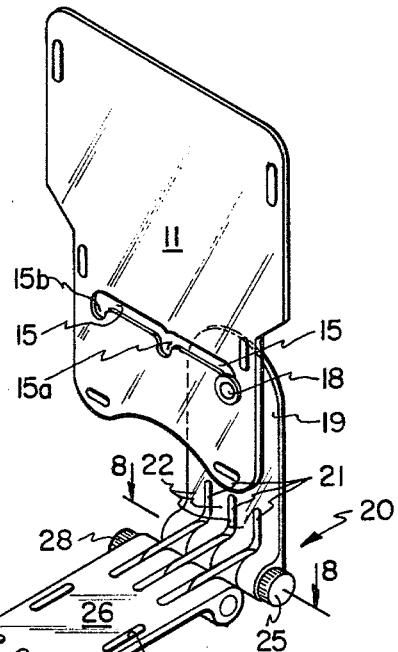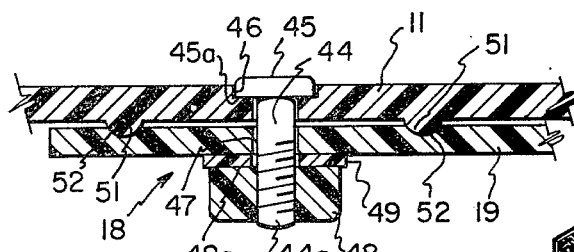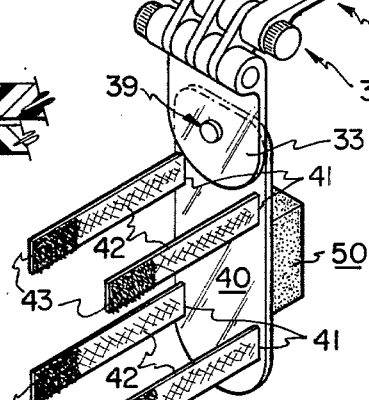

UNIVERSAL SPLINT

FIELD OF THE INVENTION

The present invention relates to splint devices for immobilizing a person's injured extremity for movement.

PRIOR ART

Heretofore, numerous devices have been developed for immobilizing a broken or injured body extremity to avoid further damage thereto, as during movement, and to facilitate the healing processes. Today, as with so many segments of our society, emergency medical care has been mechanized and automated to increase the efficiency of those services. Most metropolitan areas and even numerous rural areas today have paramedic services available that provide rapid response to an injured or sick person. Numerous devices have heretofore been developed to facilitate such dispensing of medical services. The present invention provides another such tool for use in the emergency medical care area and is particularly suited for paramedic and like operations to immobilize an injury to a person's extremity with minimal movement of the extremity during splinting.

Splints for immobilizing injured extremities have long been known and in common use. For example, a British patent No. 105,419, by Lewis, shows a hinged board configuration that is capable of being locked by turning appropriate wing nuts that lock sliding tab members in place. The hinge arrangement of the Lewis patent is, however, unlike that of the present invention in that the hinges themselves do not lock as do those of the present invention. Further, the Lewis arrangement does not involve a double hinge arrangement and pivot couplings to provide for movement in three planes as does the present invention.

Further, arrangements of arm splints with a backboard are not new, one such device shown in a patent by Longfellow, U.S. Pat. No. 2,237,252, and the use of velcro as strap fasteners to releasably hold a splint to a patient is also not new, as such was shown in a patent by Sterling, U.S. Pat. No. 4,019,504. While these devices, of course, have some elements in common with the present invention, neither of these devices involves either double hinge and pivot configuration or the particular extremity support member configuration of the present invention.

The present invention unlike any splint configuration known to the present inventor, provides a capability for adjusting the extremity support member thereof to any attitude within the three intersecting planes and locking the member in that attitude, enabling a splinting with little movement of the injured extremity, in place. While certain earlier devices such as those shown in United States Patents by Gazeley, et al., U.S. Pat. No. 2,661,000; Cornne, U.S. Pat. No. 4,050,456; and Franke, U.S. Pat. No. 4,054,130, have involved locking arrangements for maintaining a desired splint attitude, none have heretofore involved locking of the double hinges and pivots themselves.

While earlier splint configurations may have certain elements and features in common with the present invention, none have heretofore provided a device that can splint an injured person's extremity in place that is simple to install and versatile in its use. Further, none of the cited devices, nor any device within my knowledge, involves a traveling pivot configuration of the present invention whereby the device can be used on either side of a person's torso or can be used with lower extremities, and can even be used to support a person's head, providing thereby a truly universal splint.

Within the knowledge of the present inventor, there has not heretofore existed a universal splint like that of the present invention, which splint is therefore believed to be both novel and unique and a significant improvement in the art.

SUMMARY OF THE INVENTION

A principle object of the present invention in a universal splint is to provide a splint that can be formed to and locked to conform to the position of a person's injured extremity for splinting such injury in place.

Another object of the present invention in a universal splint is to provide a splint that can be adjusted and locked in any attitude to conform to the position of an injured person's extremity, including the person's head and neck.

Another object of the present invention in a universal splint is to provide board members for supporting a person's injured extremity that are appropriately double hinged and pivot coupled to provide movement within three intersecting axis or planes so as to be capable of conforming to the position of the injured extremity for splinting in place, which double hinges and pivots can be individually locked in place.

Still another object of the present invention in a universal splint is to provide a convenient attachment arrangement for maintaining the device to a person's torso.

Still another object of the present invention in a universal splint is to provide a splint that is simple and inexpensive to construct and maintain, is easy to install to a person and will conform to any extremity, including a person's head and neck, for attachment thereto to immobilize that extremity.

Principle features of the present invention in a universal splint include a backboard portion which has appropriate slots formed therein. The slots receive straps therethrough for coupling, at their ends, across the person's shoulders or hips, depending on the extremity to be supported, or the backboard can be attached, by the straps to a conventional body backboard arrangement. Across the backboard portion therein is preferably formed an elongated opening wherein a moving pivot is arranged for travel, which pivot connects to a first board to rotate freely in a plane parallel to the plane of the backboard portion. The first board forms an upper portion of an extremity supporting portion of the universal splint and connects, by a double hinge arrangement, to an upper arm board. So arranged, the upper arm board can rotate through three hundred and sixty degrees (360°) and, of course, the pivot coupling also provides for a full circle of rotation. Movement is thereby allowed in three planes that intersect at ninety degree (90°) angles. Both the double hinge coupling and the pivot are arranged to lock to form a rigid member for supporting the upper portion of an extremity and are preferably provided with slots wherethrough straps can be arranged.

To the upper arm board, by a second locking double hinge arrangement, a forearm pivot board is connected that in turn is connected by a locking pivot to a forearm board. So arranged, the forearm board is free to assume any angular attitude with respect to the upperarm board, can be locked in that attitude, preferably includes double hinges that can also be locked, straps for securing it to a person's extremity.

The described elongated opening in backboard portions provide for movement of the extremity supporting portion thereacross to support either right or left side extremities. Also, by appropriate positioning of the backboard portion, the extremity supporting portion can be used to splint legs also and so the upper arm and forearm boards should be taken as referring to thigh and calf also.

Also, by appropriate centering of the pivot coupling of the first board to the backboard portion in the elongate track and appropriate folding of the upperarm over board the forearm board, and locking of the double hinge couplings and pivots, the extremity supporting portion can be used to support a person's head and neck.

Additional features and objects of the present invention in a universal splint will become more apparent from the following detailed description, taken together with the accompanying drawings.

THE DRAWINGS

FIG. 1, is a profile perspective view of a preferred embodiment of the present invention in a universal splint;

FIG. 2, a front profile view of a person wearing the universal splint of FIG. 1;

FIG. 3, a back view of a person wearing the universal splint of FIG. 1, that is shown as having been arranged to support that person's head and neck;

FIG. 4, a profile view of an extremity supporting portion of the universal splint of FIG. 4 folded back on itself against a backboard portion thereof;

FIG. 5, a back view of the universal splint of FIG. 1, showing a first board of an extremity support portion moved to a centered attitude in an elongate opening that is formed across the backboard portion;

FIG. 6, a sectional view taken along the line 6—6 of FIG. 5, showing a preferred pivot lock configuration;

FIG. 7, a view of the universal splint of FIG. 1, where the universal splint has been rotated for attachment to a person's lower trunk area for splinting a lower extremity; and FIG. 8, a sectional view taken along the line 8—8 of FIG. 7, showing a preferred hinge lock configuration.

DETAILED DESCRIPTION

Referring now to the drawings:

FIG. 1 shows a preferred embodiment of a universal splint 10 of the present invention, hereinafter referred to as splint. Shown therein, splint 10 consists of a backboard portion 11, that includes appropriate slots or openings 12 formed therein to receive straps 13 that are coupled at their ends to maintain the backboard portion to a trunk portion of a person 14, as shown best in FIG. 2. To provide that strap end coupling velcro strips 13a, or the like, are secured thereto. Shown also in FIGS. 1, 3, 5 and 7, backboard portion 11 preferably has an elongate opening 15 formed thereacross that has a center notch 15a and end notches 15b formed therein. The elongate opening 15 provides a race, as shown best in FIGS. 1, 5 and 7, for a pivot 18 is arranged therein that couples to an extremity support portion 16. As shown in FIGS. 1 and 7, by appropriate coupling of backboard portion 11 to a person's upper or lower torso, the splint 10 can be used to splint arms or legs, with the pivot 18 moved across the elongate opening 15 for either left or right side splinting. Further, as will be explained in detail later herein, as shown in FIG. 3, by maintaining the pivot 18 in elongate opening notch 15a, and appropriately folding and locking the extremity supporting portion 16, the present invention can be used to immobilize a person's head and neck. The splint 10 can thereby be arranged to immobilize both arms, legs and a person's head and neck, functioning as a truly universal splint.

Pivot 18, as shown best in FIGS. 3, 4, 5, 6 and 7, connects a first board hinge 19 to backboard portion 11 to provide thereto three hundred and sixty degree (360°) freedom of rotation. To the first board 19, across an end thereof opposite to pivot 18, is arranged a double hinge arrangement 20 that connects to an upper arm board 26. Double hinge arrangement 20 as shown best in FIGS. 1, 2, 3, 7 and 8, is formed by slotting the first board 19 end longitudinally at 21, forming thereby fingers 22 that have aligned pin openings 23, shown best in FIG. 8, formed therethrough, as shown best in FIG. 8. Shown best in FIG. 8, tabs 24 are provided to fit in slots 21, between fingers 22, that have holes 24a formed in one end thereof to align with opening 23 in Fingers 22. So arranged, the aligned pin openings 23 and holes 24a will accommodate a pin 25 installed therein to form a first hinge. A second hinge of the double hinge arrangement 20 is provided by slotting at 27 the upper arm board 26, as shown best in FIGS. 1, 7 and 8, forming fingers 28. Fingers 28, like the described fingers 22, include openings therethrough that align with one another and openings 24b in the other tab 24 end that are installed in slots 27. So arranged, by installing a pin 29, as shown best in FIG. 8, therethrough the second hinge of the double hinge arrangement 20 is provided.

As shown best in FIG. 8, pin 25 and, it should be understood that both pins 25 and 29 include threads thereon, like threads 25a shown on an end of pin 25, which threads are for turning into a threaded portion 23b of an opening 23 through a finger 22. So arranged, by appropriately turning a head end 25b or 29b of pins 25 or 29, the threaded ends thereof will turn in the threaded portions of fingers 22 and 28 to squeeze the fingers towards one another binding against tab 24 ends, to provide a hinge locking.

Obviously, if the fingers 22 and 28 are intended to be squeezed together to bind against the opposite faces of tabs 24 and are integral to the first board and upper arm board, as shown in FIG. 8, they need to be fabricated from a material such as a plastic or metal, that has sufficient elasticity to allow for such bending but will return the finger to their original configuration or attitude after the bending force is removed.

The described pivot 18 double hinge arrangement 20 provide for essentially three hundred and sixty degrees (360°) of arc of travel of the first board 19 with the backboard portion 11 and the first board with the upper arm board 26, thereby providing for a full freedom of movement for adjusting the upper portion of the extremity supporting portion 16 to conform to for splinting in place a person's injured extremity in any attitude.

Shown in FIGS. 2 and 7, upper arm board 26 preferably includes slots 30 formed therein to accommodate a strap 31, as shown in FIG. 2, that is like straps 13 and can be fastened around the injured extremity.

The above-described double hinge arrangement 20 for coupling ends of the first board 19 and forearm board 26 should be understood to be exactly like and function like a second double hinge arrangement 32 that is shown in FIGS. 1, 2, 3 and 7. The second double hinge arrangement 32 provides a double hinge connection of the upper arm board 26 to a forearm pivot board 33. The second double hinge arrangement 32, as shown in FIG. 1, should be understood to also include fingers 34 and 35 that are formed in the respective upper arm board forearm pivot board ends, and include tabs 36 arranged therebetween with, respectively, pins 37 and 38 installed therethrough. As with pins 25 and 29, pins 37 and 38 are also threaded and turned appropriately into fingers 34 and 35 to squeeze those fingers together against tabs 36 to also provide the described friction lock. So arranged, the upper arm board 26, and the forearm pivot board 33 can thereby be moved with respect to one another through three hundred and sixty degrees (360°). The forearm pivot board 33, as shown best in FIGS. 1, 4 and 7, connects by a pivot 39 to a forearm board 40 to provide for a three hundred and sixty degree (360°) rotation capability of the one board to the other. As with the described upper arm board 26, slots or openings 41 are preferably provided in the forearm board 40 to accommodate straps 42 that preferably have velcro strips 45, or like connectors, fixed to the ends thereof for joining the strap ends around an extremity.

Like the described double hinges 20 and 32, the pivots 18 and 39 are preferably arranged to be lockable in a selected attitude, and a preferred pivot lock configuration is shown in FIG. 6. A description of one pivot should be taken as a description of the other also. Pivot 18, as shown best in FIG. 6, preferably consists of a spindle 44 that has a head 45, which spindle is installed in a recess 46 that is formed in backboard portion 11. Spindle 44 is threaded on its end 44a and is fitted through the elongate opening 15 and through an opening 47 formed through the first board 19 for turning into a nut 48. A washer 49 can be included between the nut 48 undersurface 48a and first board 19, and nut 48 can be shaped appropriately for manual turning. Also, the undersurfaces 48a and 45a of nut 48 and spindle head 45, respectively, can be appropriately scored, or the like, for increasing the efficiency of a friction coupling provided by tightening nut 48 on spindle 44. Further, spindle head 45 can be appropriately shaped as with a hexagonal head, or the like, to just fit within an appropriately formed recess 46, preventing thereby spindle 44 turning when nut 48 is turned. Pivots 18 and 39, like double hinges 20 and 32 can thereby be locked in place as when the extremity support portion 16 is adjusted to fit an injured extremity for splinting in place that extremity.

The above description, of course, is illustrative of operation of splint 10 for adjustment to an injured arm or leg, and locking the elements of the extremity support portion 16 together for splinting in place that injury. As detailed earlier herein, the pivot 18 that is arranged in elongate opening 15 is free thereby to travel across the backboard portion 11, for arrangement with either a right or left side extremity. Further, as shown best in FIGS. 1 and 3, pivot 18 can be installed in center notch 15a of elongate opening 15 and the extremity support portion 16 folded appropriately as for storage or transport, as shown best in FIG. 4. FIG. 4, of course, shows the first board 19 and upper arm board 26 folded towards one another around double hinge 20, and the upper arm board 26, forearm pivot and forearm boards 33 and 40 also folded towards one another at double hinge 32. Also, as shown in FIG. 6, to facilitate maintaining the first board 19 to backboard portion 11 as for storage and transport, the present invention further includes detents 51 formed in backboard portion 11 that fit into depressions 52 formed in first board 19, that aid in maintaining the two boards together when pivot 18 is locked appropriately.

As shown best in FIG. 3, with pivot 18 positioned in center notch 15a, the extremity support portion 16 can be folded and locked in a head and neck supporting attitude. As shown therein, with extremity support member 16 erected to a head and neck supporting attitude, strap 31 can then be secured around the upper head of person 14, which head and upper neck is shown resting against a pad 50 that is preferably fixed, as shown best in FIGS. 1, 2, 4 and 7, to a forward face 40a of forearm board 40.

As shown and described with respect to FIGS. 1 through 8, splint 10 can be arranged for installation to a person's upper or lower torso areas and can be adjusted for splinting in place either a right or left side arm or leg, and can be adjusted to be useful for immobilizing a person's head and neck. As the present invention can be adjusted for immobilizing either an arm or leg, it should therefore be understood that references in the present disclosure to upper arm and forearm should be taken as also being appropriate to thigh and calf and to upper and lower extremity, and the references to upper arm and forearm should not be taken as in any way limiting the disclosure.

As described earlier herein, the combination of pivots and double hinge arrangement of the present invention provides for an adjustment capability thereto whereby an injured extremity can be immobilized in place. While the described compression locking of the double hinge and pivot elements is preferred, it should be understood that other locking arrangements could be employed to rigidize the adjusted extremity support portion within the scope of this disclosure. The present disclosure should, therefore, be understood to not be limited to any particular locking configuration or configurations. While a preferred embodiment of the universal splint of the present invention has been shown and described herein, it should be understood that the present disclosure is made by example only, and that variations are possible without departing from the subject matter, coming within the scope and spirit of the following claims, which claims I regard as my invention.

I claim:
1. A universal splint comprising,
a backboard that includes strap means for securing it across a person's back;
an extremity support arranged for attachment to said backboard that consists of,
an upper arm board;
a forearm board;
first pivot coupling means that includes a pivot and connects said upper arm board to said backboard and is arranged to travel across said backboard to provide for positioning said extremity support to extend from either backboard side and provides a capability for locking said extremity upper arm board with respect to said backboard;
second pivot coupling means that includes a pivot and connects between said upper arm and forearm boards for providing full circle rotation capability of the one board across the other and provides for locking of the one board with respect to the other;

hinge means for arrangement with each said first and second pivot coupling means for providing a full circle rotation capability of said upper arm board towards said backboard and of said upper arm board towards said forearm board wherein the axis of said rotation is at a normal angle to the axis of rotation of each said pivot, and includes locking means for prohibiting hinge operation, at least one of which locking means includes;

fingers that extend, respectively, from a pivot coupling means and an end of said upper arm board;

tab means for interdigitating with said fingers;

holes formed appropriately through said fingers and tab means for providing, when properly aligned, a passage therethrough;

pin means for installation in the passage formed through said aligned fingers and tab means;

means for clamping the interdigitated fingers and the tab means together; and means for fastening said extremity support to a person's extremity.

2. A universal splint as recited in claim 1, wherein the first and second pivot coupling means each consist of, a straight spindle that includes a head on one end thereof with threads formed on the other;

a board that includes, proximate to one end thereof, said spindle fitted therethrough, with the hinge means arranged at the other board end; and nut means for turning into the threaded end of each said straight spindle.

3. A universal splint as recited in claim 1, wherein the clamping means consists of, each pin means is a straight shaft that includes a head on one end thereof, which shaft is threaded at the other end; and a hole through a finger of each of the boards is threaded to receive said shaft threaded end turned therein.

4. A universal splint as recited in claim 1, wherein the strap means consists of, straps fitted through appropriate slots formed in said backboard; and the strap ends include fasteners for maintaining said strap ends together.

5. A universal splint as recited in claim 4, wherein the strap end fasteners are velcro strips.

6. A universal splint as recited in claim 1, wherein the means for fastening said extremity support to a person's extremity consists of, straps fitted through appropriate slots formed in said upper arm and forearm boards; and the strap ends include fasteners for maintaining said strap ends together.

7. A universal splint as recited in claim 6, wherein,
the strap end fasteners are velcro strips.

8. A universal splint as recited in claim 1, further including, a pad means secured to a forearm board face for supporting a person's head and neck when the upper arm and forearm boards are arranged appropriately.

9. A universal splint as recited in claim 1, further including an elongate slot formed across said backboard wherein is arranged the pivot of the first pivot coupling means.

10. A universal splint as recited in claim 1, wherein both hinge means are double hinges that each include independent hinge locking consisting of, fingers that extend from both first and second pivot coupling means and from opposite ends of the upper arm board;

tab means for interdigitating with said fingers;

holes formed appropriately through said fingers and tab means for providing, when properly aligned, a passage therethrough;

pin means for installation in the passage through said aligned fingers and tab means; and means for clamping the interdigitated fingers and tab means together.

11. A universal splint as recited in claim 10, wherein the clamping means consists of, each pin means is a straight shaft that includes a head on one end thereof, which shaft is threaded at the other end; and a hole through a finger of each of the boards is threaded to receive said shaft threaded end turned therein.

* * * * *